(12) United States Patent
Shah et al.

(10) Patent No.: US 8,177,791 B2
(45) Date of Patent: *May 15, 2012

(54) EMBOLIC PROTECTION GUIDE WIRE

(75) Inventors: Niraj A. Shah, Mountain View, CA (US); Joann Heberer, Redwood, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 452 days.

This patent is subject to a terminal disclaimer.

(21) Appl. No.: 12/424,363

(22) Filed: Apr. 15, 2009

(65) Prior Publication Data
US 2009/0254118 A1    Oct. 8, 2009

Related U.S. Application Data

(63) Continuation of application No. 11/114,932, filed on Apr. 26, 2005, now Pat. No. 7,537,598, which is a continuation of application No. 09/615,157, filed on Jul. 13, 2000, now Pat. No. 6,964,670.

(51) Int. Cl.
*A61M 29/00* (2006.01)
*A61F 11/00* (2006.01)
(52) U.S. Cl. ...................... 606/108; 623/1.11
(58) Field of Classification Search .................. 606/108, 606/200; 623/1.11
See application file for complete search history.

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |

(Continued)

FOREIGN PATENT DOCUMENTS

EP    0427429 A3    9/1991

(Continued)

OTHER PUBLICATIONS

Dilitation of the Carotid Artery by a Temporary Carotid Filter by A. Beck, St. Milic, A.M. Spagnoli, November-December Issue of OPLITAI, An International Journal on Military Medicine and Health Emergencies, pp. 67-74.

(Continued)

*Primary Examiner* — Vy Q Bui
(74) *Attorney, Agent, or Firm* — Fulwider Patton LLP; Abbott Vascular; Jonathan Feuchtwang

(57) ABSTRACT

A sheath attached to a guide wire, a tubular shaft member slidable on the guide wire and a filtering assembly constricted within the sheath are movable in a vessel to a position distal to a lesion in the direction of fluid flow. The filtering assembly may be formed from a plurality of angularly spaced splines and a mesh disposed on the splines having properties of passing fluid in the vessel while blocking the passage of emboli in the fluid. The splines may be provided with shape memory for expanding against the wall of the vessel when released from constriction by the sheath. The sheath may be moved relative to the filtering assembly and the support member to release the filter for expansion against the vessel wall. An interventional device can be used to treat the lesion. Any emboli released into the vessel as a result of the interventional treatment are blocked by the filter member while fluid is allowed to pass there through.

8 Claims, 4 Drawing Sheets

U.S. PATENT DOCUMENTS

| | | | |
|---|---|---|---|
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,613,981 A | 3/1997 | Boyle et al. |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,214,040 B1 | 4/2001 | Jayaraman |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |

| Patent | Type | Date | Inventor |
|---|---|---|---|
| 6,319,242 | B1 | 11/2001 | Patterson et al. |
| 6,319,268 | B1 | 11/2001 | Ambrisco et al. |
| 6,325,815 | B1 | 12/2001 | Kusleika et al. |
| 6,336,934 | B1 | 1/2002 | Gilson et al. |
| 6,340,364 | B2 | 1/2002 | Kanesaka |
| 6,340,465 | B1 | 1/2002 | Hsu et al. |
| 6,346,116 | B1 | 2/2002 | Brooks et al. |
| 6,348,056 | B1 | 2/2002 | Bates et al. |
| 6,355,051 | B1 | 3/2002 | Sisskind et al. |
| 6,361,545 | B1 | 3/2002 | Macoviak et al. |
| 6,361,546 | B1 | 3/2002 | Khosravi |
| 6,364,895 | B1 | 4/2002 | Greenhalgh |
| 6,364,896 | B1 | 4/2002 | Addis |
| 6,364,900 | B1 | 4/2002 | Heuser |
| 6,371,969 | B1 | 4/2002 | Tsugita et al. |
| 6,371,970 | B1 | 4/2002 | Khosravi et al. |
| 6,371,971 | B1 | 4/2002 | Tsugita et al. |
| 6,375,670 | B1 | 4/2002 | Greenhalgh |
| 6,383,206 | B1 | 5/2002 | Gillick et al. |
| 6,384,062 | B1 | 5/2002 | Ikeda et al. |
| 6,391,044 | B1 | 5/2002 | Yadav et al. |
| 6,394,978 | B1 | 5/2002 | Boyle et al. |
| 6,395,014 | B1 | 5/2002 | Macoviak et al. |
| 6,398,756 | B2 | 6/2002 | Peterson et al. |
| 6,402,771 | B1 | 6/2002 | Palmer et al. |
| 6,406,471 | B1 | 6/2002 | Jang et al. |
| 6,423,032 | B2 | 7/2002 | Parodi |
| 6,423,086 | B1 | 7/2002 | Barbut et al. |
| 6,425,909 | B1 | 7/2002 | Dieck et al. |
| 6,428,559 | B1 | 8/2002 | Johnson |
| 6,432,122 | B1 | 8/2002 | Gilson et al. |
| 6,436,121 | B1 | 8/2002 | Blom |
| 6,443,926 | B1 | 9/2002 | Kletschka |
| 6,443,971 | B1 | 9/2002 | Boylan et al. |
| 6,443,972 | B1 | 9/2002 | Bosma et al. |
| 6,443,979 | B1 | 9/2002 | Stalker et al. |
| 6,447,530 | B1 | 9/2002 | Ostrovsky et al. |
| 6,447,531 | B1 | 9/2002 | Amplatz |
| 6,450,989 | B2 | 9/2002 | Dubrul et al. |
| 6,458,139 | B1 | 10/2002 | Palmer et al. |
| 6,461,370 | B1 | 10/2002 | Gray et al. |
| 6,468,291 | B2 | 10/2002 | Bates et al. |
| 6,482,222 | B1 | 11/2002 | Bruckheimer et al. |
| 6,485,456 | B1 | 11/2002 | Kletschka |
| 6,485,497 | B2 | 11/2002 | Wensel et al. |
| 6,485,500 | B1 | 11/2002 | Kokish et al. |
| 6,485,501 | B1 | 11/2002 | Green |
| 6,485,502 | B2 | 11/2002 | Don Michael et al. |
| 6,485,507 | B1 | 11/2002 | Walak et al. |
| 6,494,895 | B2 | 12/2002 | Addis |
| 6,499,487 | B1 | 12/2002 | McKenzie et al. |
| 6,500,166 | B1 | 12/2002 | Zadno Azizi et al. |
| 6,506,203 | B1 | 1/2003 | Boyle et al. |
| 6,506,205 | B2 | 1/2003 | Goldberg et al. |
| 6,511,492 | B1 | 1/2003 | Rosenbluth |
| 6,511,496 | B1 | 1/2003 | Huter et al. |
| 6,511,497 | B1 | 1/2003 | Braun et al. |
| 6,511,503 | B1 | 1/2003 | Burkett et al. |
| 6,514,273 | B1 | 2/2003 | Voss et al. |
| 6,517,550 | B1 | 2/2003 | Konya et al. |
| 6,517,559 | B1 | 2/2003 | O'Connell |
| 6,520,978 | B1 | 2/2003 | Blackledge et al. |
| 6,527,746 | B1 | 3/2003 | Oslund et al. |
| 6,527,791 | B2 | 3/2003 | Fisher |
| 6,530,939 | B1 | 3/2003 | Hopkins et al. |
| 6,530,940 | B2 | 3/2003 | Fisher |
| 6,533,800 | B1 | 3/2003 | Barbut |
| 6,537,294 | B1 | 3/2003 | Boyle et al. |
| 6,537,295 | B2 | 3/2003 | Petersen |
| 6,537,296 | B2 | 3/2003 | Levinson et al. |
| 6,537,297 | B2 | 3/2003 | Tsugita et al. |
| 6,540,722 | B1 | 4/2003 | Boyle et al. |
| 6,540,767 | B1 | 4/2003 | Walak et al. |
| 6,540,768 | B1 * | 4/2003 | Diaz et al. ............... 606/200 |
| 6,544,276 | B1 | 4/2003 | Azizi |
| 6,544,279 | B1 | 4/2003 | Hopkins et al. |
| 6,544,280 | B1 | 4/2003 | Daniel et al. |
| 6,547,759 | B1 | 4/2003 | Fisher |
| 6,551,268 | B1 | 4/2003 | Kaganov et al. |
| 6,551,341 | B2 | 4/2003 | Boylan et al. |
| 6,551,342 | B1 | 4/2003 | Shen et al. |
| 6,558,401 | B1 | 5/2003 | Azizi |
| 6,558,405 | B1 | 5/2003 | McInnes |
| 6,562,058 | B2 | 5/2003 | Seguin |
| 6,565,591 | B2 | 5/2003 | Kelly et al. |
| 6,569,184 | B2 | 5/2003 | Huter |
| 6,575,995 | B1 | 6/2003 | Huter et al. |
| 6,575,996 | B1 | 6/2003 | Denison et al. |
| 6,575,997 | B1 | 6/2003 | Palmer et al. |
| 6,582,447 | B1 | 6/2003 | Patel et al. |
| 6,582,448 | B1 | 6/2003 | Boyle et al. |
| 6,585,756 | B1 | 7/2003 | Strecker |
| 6,589,263 | B1 | 7/2003 | Hopkins et al. |
| 6,589,265 | B1 | 7/2003 | Palmer et al. |
| 6,592,546 | B1 | 7/2003 | Barbut et al. |
| 6,592,606 | B2 | 7/2003 | Huter et al. |
| 6,592,607 | B1 | 7/2003 | Palmer et al. |
| 6,592,616 | B1 | 7/2003 | Stack et al. |
| 6,596,011 | B2 | 7/2003 | Johnson et al. |
| 6,599,307 | B1 | 7/2003 | Huter et al. |
| 6,599,308 | B2 | 7/2003 | Amplatz |
| 6,602,269 | B2 | 8/2003 | Wallace et al. |
| 6,602,271 | B2 | 8/2003 | Adams et al. |
| 6,602,272 | B2 | 8/2003 | Boylan et al. |
| 6,602,273 | B2 | 8/2003 | Marshall |
| 6,605,102 | B1 | 8/2003 | Mazzocchi et al. |
| 6,605,111 | B2 | 8/2003 | Bose et al. |
| 6,607,506 | B2 | 8/2003 | Kletschka |
| 6,610,077 | B1 | 8/2003 | Hancock et al. |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,682 | B2 | 9/2003 | Joergensen et al. |
| 6,620,148 | B1 | 9/2003 | Tsugita et al. |
| 6,620,182 | B1 | 9/2003 | Khosravi |
| 6,623,450 | B1 | 9/2003 | Dutta |
| 6,629,953 | B1 | 10/2003 | Boyd |
| 6,632,236 | B2 | 10/2003 | Hogendijk |
| 6,632,241 | B1 | 10/2003 | Hancock et al. |
| 6,635,068 | B1 | 10/2003 | Dubrul et al. |
| 6,635,070 | B2 | 10/2003 | Leeflang et al. |
| 6,638,293 | B1 | 10/2003 | Makowner et al. |
| 6,638,294 | B1 | 10/2003 | Palmer |
| 6,645,220 | B1 | 11/2003 | Huter et al. |
| 6,645,221 | B1 | 11/2003 | Richter |
| 6,645,223 | B2 | 11/2003 | Boyle et al. |
| 6,645,224 | B2 | 11/2003 | Gilson et al. |
| 6,652,480 | B1 | 11/2003 | Imran et al. |
| 6,652,505 | B1 | 11/2003 | Tsugita et al. |
| 6,652,554 | B1 | 11/2003 | Wholey et al. |
| 6,652,557 | B1 | 11/2003 | MacDonald |
| 6,656,202 | B2 | 12/2003 | Papp et al. |
| 6,656,203 | B2 | 12/2003 | Roth et al. |
| 6,656,204 | B2 | 12/2003 | Ambrisco et al. |
| 6,656,351 | B2 | 12/2003 | Boyle |
| 6,660,021 | B1 | 12/2003 | Palmer et al. |
| 6,663,650 | B2 | 12/2003 | Sepetka et al. |
| 6,663,651 | B2 | 12/2003 | Krolik et al. |
| 6,663,652 | B2 | 12/2003 | Daniel et al. |
| 6,673,090 | B2 | 1/2004 | Root et al. |
| 6,676,666 | B2 | 1/2004 | Vrba et al. |
| 6,676,682 | B1 | 1/2004 | Tsugita et al. |
| 6,676,683 | B1 | 1/2004 | Addis |
| 6,679,902 | B1 | 1/2004 | Boyle et al. |
| 6,679,903 | B2 | 1/2004 | Kurz |
| 6,682,546 | B2 | 1/2004 | Amplatz |
| 6,685,722 | B1 | 2/2004 | Rosenbluth et al. |
| 6,689,151 | B2 | 2/2004 | Becker et al. |
| 6,692,513 | B2 | 2/2004 | Streeter et al. |
| 6,695,813 | B1 | 2/2004 | Boyle et al. |
| 6,695,858 | B1 | 2/2004 | Dubrul et al. |
| 6,695,864 | B2 | 2/2004 | Macoviak et al. |
| 6,696,666 | B2 | 2/2004 | Merdan et al. |
| 6,699,260 | B2 | 3/2004 | Dubrul et al. |
| 6,702,834 | B1 | 3/2004 | Boyle et al. |
| 6,706,055 | B2 | 3/2004 | Douk et al. |
| 6,712,834 | B2 | 3/2004 | Yassour et al. |
| 6,712,835 | B2 | 3/2004 | Mazzocchi et al. |

| | | | | | | |
|---|---|---|---|---|---|---|
| 6,716,231 B1 | 4/2004 | Rafiee et al. | | 6,994,718 B2 | 2/2006 | Groothuis et al. |
| 6,723,085 B2 | 4/2004 | Jang et al. | | 6,997,938 B2 | 2/2006 | Wang et al. |
| 6,726,701 B2 | 4/2004 | Gilson | | 6,997,939 B2 | 2/2006 | Linder et al. |
| 6,726,702 B2 | 4/2004 | Khosravi | | 7,001,406 B2 | 2/2006 | Eskuri et al. |
| 6,726,703 B2 | 4/2004 | Broome et al. | | 7,001,407 B2 | 2/2006 | Hansen et al. |
| 6,740,061 B1 | 5/2004 | Oslund et al. | | 7,004,954 B1 | 2/2006 | Voss et al. |
| 6,743,247 B1 | 6/2004 | Levinson et al. | | 7,004,955 B2 | 2/2006 | Shen et al. |
| 6,746,469 B2 | 6/2004 | Mouw | | 7,004,956 B2 | 2/2006 | Palmer et al. |
| 6,752,819 B1 | 6/2004 | Brady et al. | | 7,004,964 B2 | 2/2006 | Thompson et al. |
| 6,755,846 B1 | 6/2004 | Yadav | | 7,011,671 B2 | 3/2006 | Welch |
| 6,758,855 B2 | 7/2004 | Fulton, III et al. | | 7,011,672 B2 | 3/2006 | Barbut et al. |
| 6,761,727 B1 | 7/2004 | Ladd | | 7,014,647 B2 | 3/2006 | Brady et al. |
| 6,773,448 B2 | 8/2004 | Kusleika et al. | | 7,018,372 B2 | 3/2006 | Casey |
| 6,790,219 B1 | 9/2004 | Murphy | | 7,018,385 B2 | 3/2006 | Bates et al. |
| 6,793,666 B2 | 9/2004 | Hansen et al. | | 7,018,393 B1 | 3/2006 | Boyle et al. |
| 6,793,668 B1 | 9/2004 | Fisher | | 7,029,440 B2 | 4/2006 | Broome et al. |
| 6,800,080 B1 | 10/2004 | Bates | | 7,033,375 B2 | 4/2006 | Mazzocchi et al. |
| 6,814,739 B2 | 11/2004 | Secrest et al. | | 7,037,320 B2 | 5/2006 | Brady et al. |
| 6,818,006 B2 | 11/2004 | Douk et al. | | 7,041,116 B2 | 5/2006 | Goto et al. |
| 6,837,898 B2 | 1/2005 | Boyle | | 7,044,958 B2 | 5/2006 | Douk et al. |
| 6,840,950 B2 | 1/2005 | Stanford et al. | | 7,048,752 B2 | 5/2006 | Mazzocchi |
| 6,843,798 B2 | 1/2005 | Kusleika et al. | | 7,048,758 B2 | 5/2006 | Boyle et al. |
| 6,846,316 B2 | 1/2005 | Abrams | | 7,056,328 B2 | 6/2006 | Arnott |
| 6,846,317 B1 | 1/2005 | Nigon | | 7,060,082 B2 | 6/2006 | Goll et al. |
| 6,863,696 B2 | 3/2005 | Kantsevitcha et al. | | 7,077,854 B2 | 7/2006 | Khosravi |
| 6,866,677 B2 | 3/2005 | Douk et al. | | 7,094,243 B2 | 8/2006 | Mulholland |
| 6,872,216 B2 | 3/2005 | Daniel et al. | | 7,094,249 B1 | 8/2006 | Broome et al. |
| 6,878,151 B2 | 4/2005 | Carrison et al. | | 7,097,440 B2 | 8/2006 | Papp et al. |
| 6,878,153 B2 | 4/2005 | Linder et al. | | 7,097,651 B2 | 8/2006 | Harrison et al. |
| 6,887,256 B2 | 5/2005 | Gilson et al. | | 7,101,379 B2 | 9/2006 | Gregory, Jr et al. |
| 6,887,257 B2 | 5/2005 | Salahieh et al. | | 7,101,380 B2 | 9/2006 | Khachin et al. |
| 6,887,258 B2 | 5/2005 | Denison | | 7,108,707 B2 | 9/2006 | Huter et al. |
| 6,888,098 B1 | 5/2005 | Merdan et al. | | 2002/0091408 A1 | 7/2002 | Sutton et al. |
| 6,890,340 B2 | 5/2005 | Duane | | 2002/0091409 A1 | 7/2002 | Sutton et al. |
| 6,890,341 B2 | 5/2005 | Dieck et al. | | 2002/0095141 A1 | 7/2002 | Belef et al. |
| 6,893,450 B2 | 5/2005 | Foster | | 2002/0099407 A1 | 7/2002 | Becker et al. |
| 6,893,451 B2 | 5/2005 | Cano et al. | | 2002/0103501 A1 | 8/2002 | Diaz et al. |
| 6,896,690 B1 | 5/2005 | Lambrecht et al. | | 2002/0107541 A1 | 8/2002 | Vale et al. |
| 6,896,691 B2 | 5/2005 | Boylan | | 2002/0111648 A1 | 8/2002 | Kusleika et al. |
| 6,902,540 B2 | 6/2005 | Dorros et al. | | 2002/0111649 A1 | 8/2002 | Russo et al. |
| 6,908,474 B2 | 6/2005 | Hogendijk et al. | | 2002/0115942 A1 | 8/2002 | Stanford et al. |
| 6,911,036 B2 | 6/2005 | Douk et al. | | 2002/0120286 A1 | 8/2002 | Dobrava et al. |
| 6,913,612 B2 | 7/2005 | Palmer et al. | | 2002/0120287 A1 | 8/2002 | Huter |
| 6,918,921 B2 | 7/2005 | Brady et al. | | 2002/0121472 A1 | 9/2002 | Garner et al. |
| 6,929,652 B1 | 8/2005 | Andrews | | 2002/0123720 A1 | 9/2002 | Kusleika et al. |
| 6,932,830 B2 | 8/2005 | Ungs | | 2002/0123755 A1 | 9/2002 | Lowe et al. |
| 6,932,831 B2 | 8/2005 | Forber | | 2002/0128679 A1 | 9/2002 | Turovskiy et al. |
| 6,936,058 B2 | 8/2005 | Forde et al. | | 2002/0128680 A1 | 9/2002 | Pavlovic |
| 6,936,059 B2 | 8/2005 | Belef | | 2002/0128681 A1 | 9/2002 | Broome et al. |
| 6,939,361 B1 | 9/2005 | Kleshinski | | 2002/0133092 A1 | 9/2002 | Oslund et al. |
| 6,939,362 B2 | 9/2005 | Boyle et al. | | 2002/0138094 A1 | 9/2002 | Borillo et al. |
| 6,942,673 B2 | 9/2005 | Bates et al. | | 2002/0138095 A1 | 9/2002 | Mazzocchi et al. |
| 6,949,103 B2 | 9/2005 | Mazzocchi et al. | | 2002/0143360 A1 | 10/2002 | Douk et al. |
| 6,951,570 B2 | 10/2005 | Linder et al. | | 2002/0143361 A1 | 10/2002 | Douk et al. |
| 6,953,471 B1 | 10/2005 | Lilly et al. | | 2002/0151927 A1 | 10/2002 | Douk et al. |
| 6,953,472 B2 | 10/2005 | Palmer et al. | | 2002/0156456 A1 | 10/2002 | Fisher |
| 6,958,074 B2 | 10/2005 | Russell | | 2002/0156457 A1 | 10/2002 | Fisher |
| 6,960,370 B2 | 11/2005 | Monni et al. | | 2002/0161390 A1 | 10/2002 | Mouw |
| 6,962,598 B2 | 11/2005 | Linder et al. | | 2002/0161392 A1 | 10/2002 | Dubrul |
| 6,964,670 B1 | 11/2005 | Shah | | 2002/0161393 A1 | 10/2002 | Demond et al. |
| 6,964,672 B2 | 11/2005 | Brady | | 2002/0161395 A1 | 10/2002 | Douk et al. |
| 6,964,673 B2 | 11/2005 | Tsugita et al. | | 2002/0165576 A1 | 11/2002 | Boyle et al. |
| 6,969,395 B2 | 11/2005 | Eskuri | | 2002/0169414 A1 | 11/2002 | Kletschka |
| 6,969,396 B2 | 11/2005 | Krolik et al. | | 2002/0169458 A1 | 11/2002 | Connors, III |
| 6,969,402 B2 | 11/2005 | Bales et al. | | 2002/0169472 A1 | 11/2002 | Douk et al. |
| 6,970,730 B2 | 11/2005 | Fuimaono et al. | | 2002/0169474 A1 | 11/2002 | Kusleika et al. |
| 6,972,025 B2 | 12/2005 | WasDyke | | 2002/0173815 A1 | 11/2002 | Hogendijk et al. |
| 6,973,340 B2 | 12/2005 | Fuimaono et al. | | 2002/0173817 A1 | 11/2002 | Kletschka et al. |
| 6,974,468 B2 | 12/2005 | DoBrava et al. | | 2002/0188313 A1 | 12/2002 | Johnson et al. |
| 6,974,469 B2 | 12/2005 | Broome et al. | | 2002/0188314 A1 | 12/2002 | Anderson et al. |
| 6,979,343 B2 | 12/2005 | Russo | | 2002/0193825 A1 | 12/2002 | McGuckin et al. |
| 6,979,344 B2 | 12/2005 | Jones et al. | | 2002/0193826 A1 | 12/2002 | McGuckin et al. |
| 6,986,778 B2 | 1/2006 | Zadno-Azizi | | 2002/0193827 A1 | 12/2002 | McGuckin et al. |
| 6,989,019 B2 | 1/2006 | Mazzocchi | | 2002/0193828 A1 | 12/2002 | Griffin et al. |
| 6,989,021 B2 | 1/2006 | Bosma et al. | | 2003/0004536 A1 | 1/2003 | Boylan et al. |
| 6,989,027 B2 | 1/2006 | Allen et al. | | 2003/0004537 A1 | 1/2003 | Boyle et al. |
| 6,991,641 B2 | 1/2006 | Diaz et al. | | 2003/0004539 A1 | 1/2003 | Linder et al. |
| 6,991,642 B2 | 1/2006 | Peterson | | 2003/0004540 A1 | 1/2003 | Linder et al. |
| RE38,972 E | 2/2006 | Purdy | | 2003/0004541 A1 | 1/2003 | Linder et al. |

| | | | | | | |
|---|---|---|---|---|---|---|
| 2003/0009188 A1 | 1/2003 | Linder et al. | | 2003/0216774 A1 | 11/2003 | Larson |
| 2003/0009189 A1 | 1/2003 | Gilson et al. | | 2003/0220665 A1 | 11/2003 | Eskuri et al. |
| 2003/0015206 A1 | 1/2003 | Roth et al. | | 2003/0225418 A1 | 12/2003 | Eskuri et al. |
| 2003/0018354 A1 | 1/2003 | Roth et al. | | 2003/0225435 A1 | 12/2003 | Huter et al. |
| 2003/0023265 A1 | 1/2003 | Forber | | 2003/0229295 A1 | 12/2003 | Houde et al. |
| 2003/0028238 A1 | 2/2003 | Burkett et al. | | 2003/0229374 A1 | 12/2003 | Brady et al. |
| 2003/0032941 A1 | 2/2003 | Boyle et al. | | 2003/0233117 A1 | 12/2003 | Adams et al. |
| 2003/0032977 A1 | 2/2003 | Brady et al. | | 2003/0236545 A1 | 12/2003 | Gilson |
| 2003/0040772 A1 | 2/2003 | Hyodoh et al. | | 2004/0002730 A1 | 1/2004 | Denison et al. |
| 2003/0042186 A1 | 3/2003 | Boyle et al. | | 2004/0006361 A1 | 1/2004 | Boyle et al. |
| 2003/0045898 A1 | 3/2003 | Harrison et al. | | 2004/0006364 A1 | 1/2004 | Ladd |
| 2003/0057156 A1 | 3/2003 | Peterson et al. | | 2004/0006365 A1 | 1/2004 | Brady et al. |
| 2003/0060782 A1 | 3/2003 | Bose et al. | | 2004/0006366 A1 | 1/2004 | Huter et al. |
| 2003/0060843 A1 | 3/2003 | Boucher | | 2004/0006367 A1 | 1/2004 | Johnson et al. |
| 2003/0060844 A1 | 3/2003 | Borillo et al. | | 2004/0006368 A1 | 1/2004 | Mazzocchi et al. |
| 2003/0065354 A1 | 4/2003 | Boyle et al. | | 2004/0015184 A1 | 1/2004 | Boyle et al. |
| 2003/0069596 A1 | 4/2003 | Eskuri | | 2004/0019363 A1 | 1/2004 | Hanson et al. |
| 2003/0069597 A1 | 4/2003 | Petersen | | 2004/0034385 A1 | 2/2004 | Gilson et al. |
| 2003/0078519 A1 | 4/2003 | Salahieh et al. | | 2004/0039411 A1 | 2/2004 | Gilson et al. |
| 2003/0078614 A1 | 4/2003 | Salahieh et al. | | 2004/0044359 A1 | 3/2004 | Renati et al. |
| 2003/0083692 A1 | 5/2003 | Vrba et al. | | 2004/0044360 A1 | 3/2004 | Lowe |
| 2003/0083693 A1 | 5/2003 | Daniel et al. | | 2004/0049226 A1 | 3/2004 | Keegan et al. |
| 2003/0100917 A1 | 5/2003 | Boyle et al. | | 2004/0059372 A1 | 3/2004 | Tsugita |
| 2003/0100918 A1 | 5/2003 | Duane | | 2004/0059373 A1 | 3/2004 | Shapiro et al. |
| 2003/0105484 A1 | 6/2003 | Boyle et al. | | 2004/0082967 A1 | 4/2004 | Broome et al. |
| 2003/0109824 A1 | 6/2003 | Anderson et al. | | 2004/0082968 A1 | 4/2004 | Krolik et al. |
| 2003/0114879 A1 | 6/2003 | Euteneuer et al. | | 2004/0088000 A1 | 5/2004 | Muller |
| 2003/0114880 A1 | 6/2003 | Hansen et al. | | 2004/0088002 A1 | 5/2004 | Boyle et al. |
| 2003/0120303 A1 | 6/2003 | Boyle et al. | | 2004/0093009 A1 | 5/2004 | Denison et al. |
| 2003/0130680 A1 | 7/2003 | Russell | | 2004/0093010 A1 | 5/2004 | Gesswein et al. |
| 2003/0130681 A1 | 7/2003 | Ungs | | 2004/0093011 A1 | 5/2004 | Vrba |
| 2003/0130682 A1 | 7/2003 | Broome et al. | | 2004/0093012 A1 | 5/2004 | Cully et al. |
| 2003/0130684 A1 | 7/2003 | Brady et al. | | 2004/0093013 A1 | 5/2004 | Brady et al. |
| 2003/0130685 A1 | 7/2003 | Daniel et al. | | 2004/0098022 A1 | 5/2004 | Barone |
| 2003/0130686 A1 | 7/2003 | Daniel et al. | | 2004/0098026 A1 | 5/2004 | Joergensen et al. |
| 2003/0130687 A1 | 7/2003 | Daniel et al. | | 2004/0098032 A1 | 5/2004 | Papp et al. |
| 2003/0130688 A1 | 7/2003 | Daniel et al. | | 2004/0098033 A1 | 5/2004 | Leeflang et al. |
| 2003/0135162 A1 | 7/2003 | Deyette, Jr. et al. | | 2004/0102807 A1 | 5/2004 | Kusleika et al. |
| 2003/0135232 A1 | 7/2003 | Douk et al. | | 2004/0106944 A1 | 6/2004 | Daniel et al. |
| 2003/0139764 A1 | 7/2003 | Levinson et al. | | 2004/0111111 A1 | 6/2004 | Lin |
| 2003/0144685 A1 | 7/2003 | Boyle et al. | | 2004/0116960 A1 | 6/2004 | Demond et al. |
| 2003/0144689 A1 | 7/2003 | Brady et al. | | 2004/0122466 A1 | 6/2004 | Bales |
| 2003/0150821 A1 | 8/2003 | Bates et al. | | 2004/0127933 A1 | 7/2004 | Demond et al. |
| 2003/0153935 A1 | 8/2003 | Mialhe | | 2004/0127934 A1 | 7/2004 | Gilson et al. |
| 2003/0153942 A1 | 8/2003 | Wang et al. | | 2004/0127936 A1 | 7/2004 | Salahieh et al. |
| 2003/0153943 A1 | 8/2003 | Michael et al. | | 2004/0138693 A1 | 7/2004 | Eskuri et al. |
| 2003/0158574 A1 | 8/2003 | Esch et al. | | 2004/0138694 A1 | 7/2004 | Tran et al. |
| 2003/0163064 A1 | 8/2003 | Vrba et al. | | 2004/0138696 A1 | 7/2004 | Drasler et al. |
| 2003/0171770 A1 | 9/2003 | Anderson et al. | | 2004/0147955 A1 | 7/2004 | Beulke et al. |
| 2003/0171771 A1 | 9/2003 | Anderson et al. | | 2004/0153118 A1 | 8/2004 | Clubb et al. |
| 2003/0171803 A1 | 9/2003 | Shimon | | 2004/0153119 A1 | 8/2004 | Kusleika et al. |
| 2003/0176884 A1 | 9/2003 | Berrada et al. | | 2004/0158275 A1 | 8/2004 | Crank et al. |
| 2003/0176885 A1 | 9/2003 | Broome et al. | | 2004/0158277 A1 | 8/2004 | Lowe et al. |
| 2003/0176886 A1 | 9/2003 | Wholey et al. | | 2004/0158278 A1 | 8/2004 | Becker et al. |
| 2003/0176889 A1 | 9/2003 | Boyle et al. | | 2004/0158279 A1 | 8/2004 | Petersen |
| 2003/0181942 A1 | 9/2003 | Sutton et al. | | 2004/0158280 A1 | 8/2004 | Morris et al. |
| 2003/0181943 A1 | 9/2003 | Daniel et al. | | 2004/0158281 A1 | 8/2004 | Boylan et al. |
| 2003/0187474 A1 | 10/2003 | Keegan et al. | | 2004/0167564 A1 | 8/2004 | Fedie |
| 2003/0187475 A1 | 10/2003 | Tsugita et al. | | 2004/0167565 A1 | 8/2004 | Beulke et al. |
| 2003/0187495 A1 | 10/2003 | Cully et al. | | 2004/0167566 A1 | 8/2004 | Beulke et al. |
| 2003/0191493 A1 | 10/2003 | Epstein et al. | | 2004/0167567 A1 | 8/2004 | Cano et al. |
| 2003/0195554 A1 | 10/2003 | Shen et al. | | 2004/0167568 A1 | 8/2004 | Boyle et al. |
| 2003/0195555 A1 | 10/2003 | Khairkhahan et al. | | 2004/0172055 A1 | 9/2004 | Huter et al. |
| 2003/0195556 A1 | 10/2003 | Stack et al. | | 2004/0176794 A1 | 9/2004 | Khosravi |
| 2003/0199819 A1 | 10/2003 | Beck | | 2004/0193208 A1 | 9/2004 | Talpade et al. |
| 2003/0199921 A1 | 10/2003 | Palmer et al. | | 2004/0199198 A1 | 10/2004 | Beulke et al. |
| 2003/0204168 A1 | 10/2003 | Bosma et al. | | 2004/0199199 A1 | 10/2004 | Krolik et al. |
| 2003/0204202 A1 | 10/2003 | Palmer et al. | | 2004/0199203 A1 | 10/2004 | Oslund et al. |
| 2003/0208222 A1 | 11/2003 | Zadno-Azizi | | 2004/0204737 A1 | 10/2004 | Boismier et al. |
| 2003/0208224 A1 | 11/2003 | Broome | | 2004/0210250 A1 | 10/2004 | Eskuri |
| 2003/0208225 A1 | 11/2003 | Goll et al. | | 2004/0220608 A1 | 11/2004 | D'Aquanni et al. |
| 2003/0208226 A1 | 11/2003 | Bruckheimer et al. | | 2004/0220609 A1 | 11/2004 | Douk et al. |
| 2003/0208227 A1 | 11/2003 | Thomas | | 2004/0220611 A1 | 11/2004 | Ogle |
| 2003/0208228 A1 | 11/2003 | Gilson et al. | | 2004/0225322 A1 | 11/2004 | Garrison et al. |
| 2003/0208229 A1 | 11/2003 | Kletschka | | 2004/0236368 A1 | 11/2004 | McGucklin, Jr. et al. |
| 2003/0212361 A1 | 11/2003 | Boyle et al. | | 2004/0236369 A1 | 11/2004 | Dubrul |
| 2003/0212429 A1 | 11/2003 | Keegan et al. | | 2004/0249409 A1 | 12/2004 | Krolik et al. |
| 2003/0212431 A1 | 11/2003 | Brady et al. | | 2004/0254601 A1 | 12/2004 | Eskuri |
| 2003/0212434 A1 | 11/2003 | Thielen | | 2004/0254602 A1 | 12/2004 | Lehe et al. |

| | | |
|---|---|---|
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salahieh et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0472334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/45592 | 6/2001 |
| WO | WO01/87183 | 11/2001 |

OTHER PUBLICATIONS

Minibasket for Percutaneous Embolectomy and Filter ProtectionAgainst Distal Embolization: Technical Note.

* cited by examiner

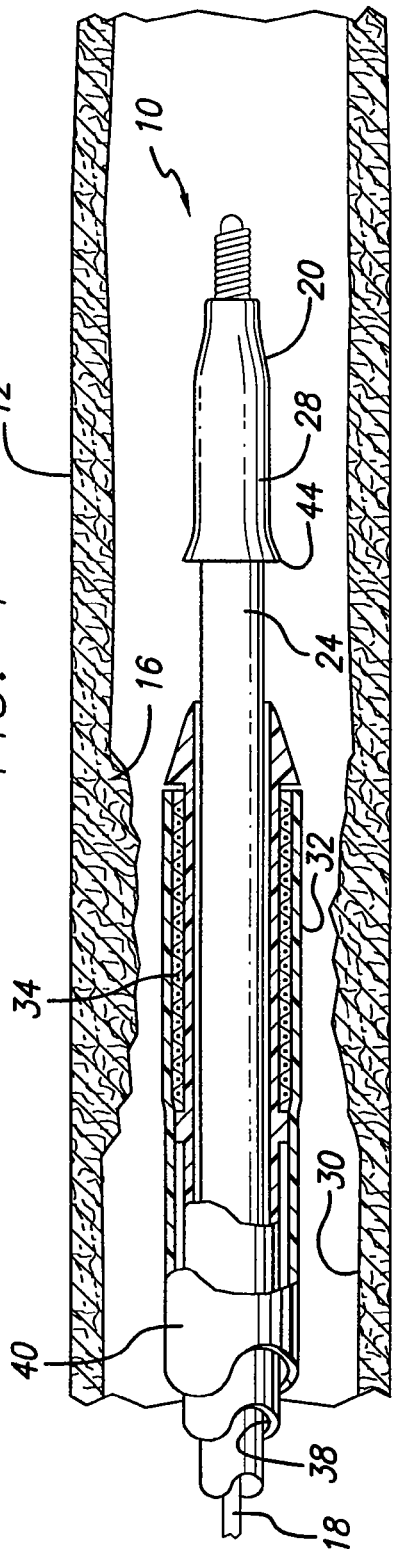
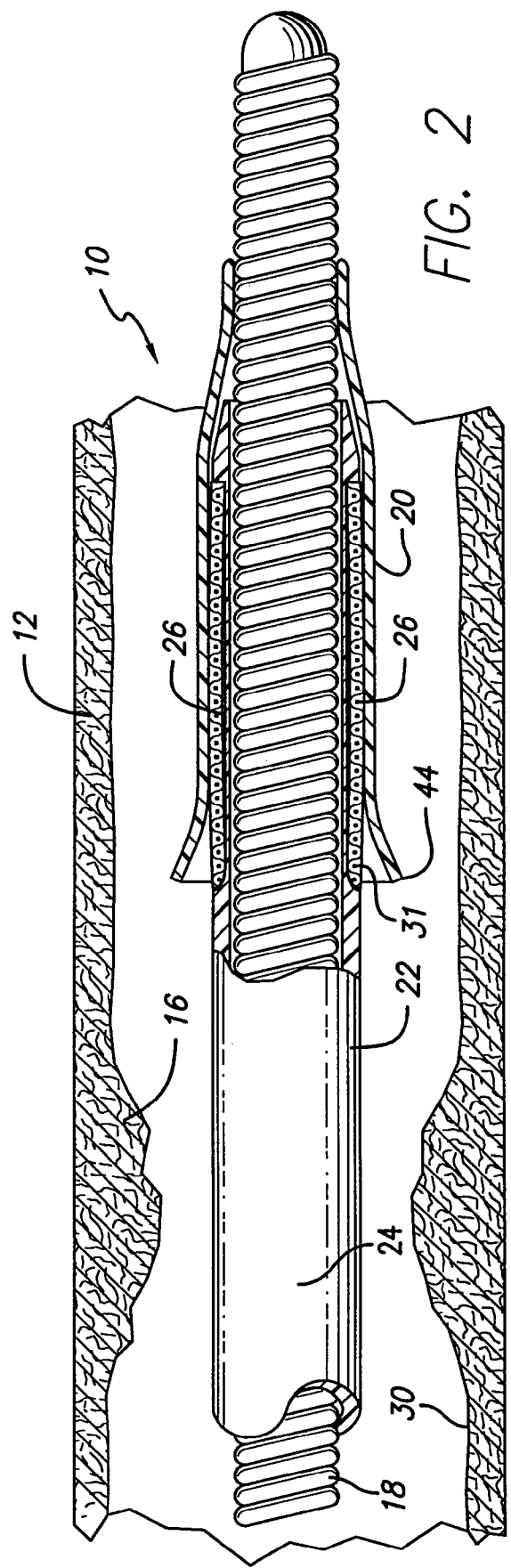

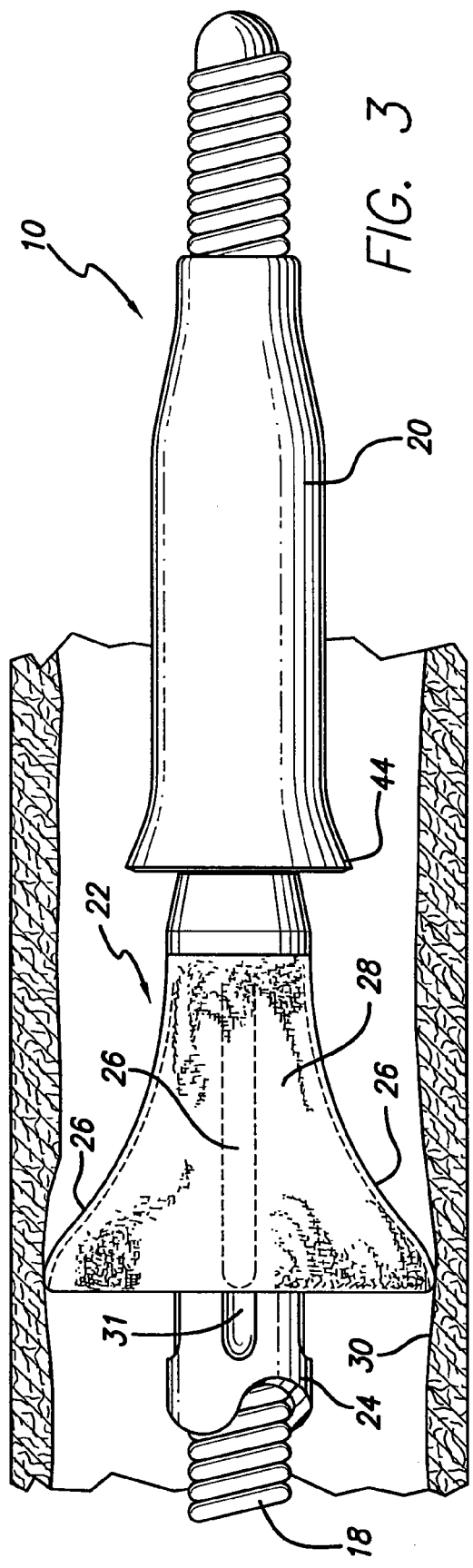
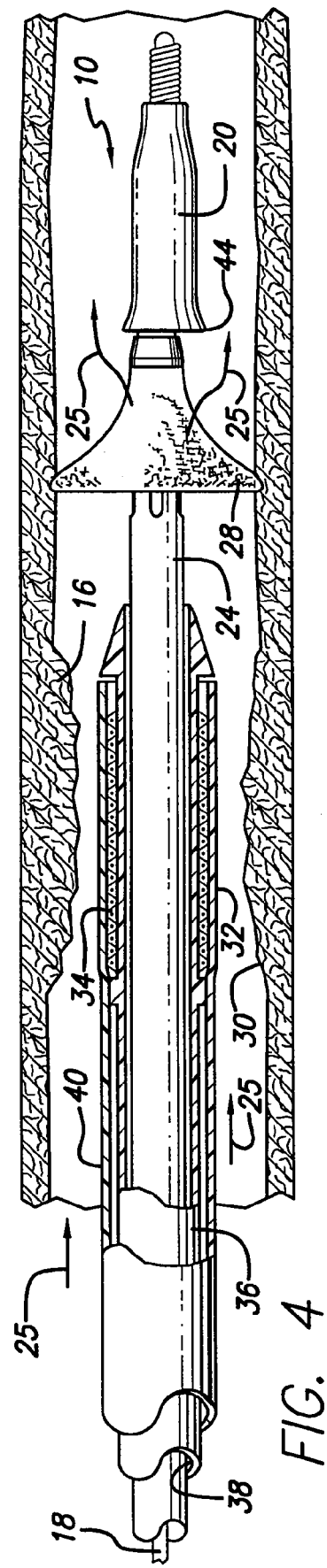

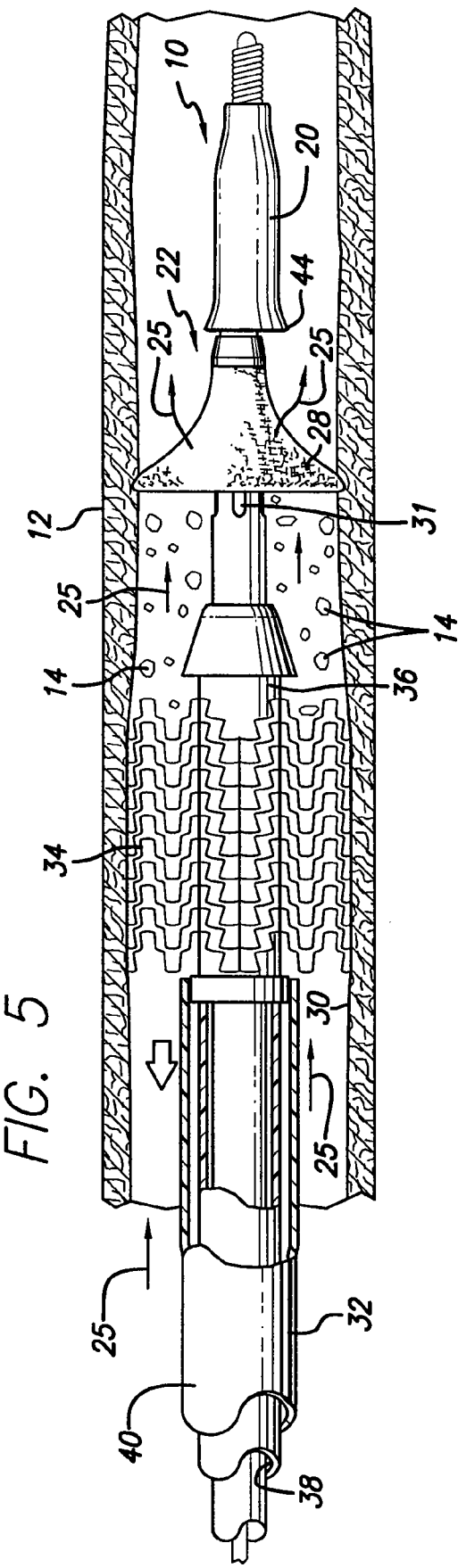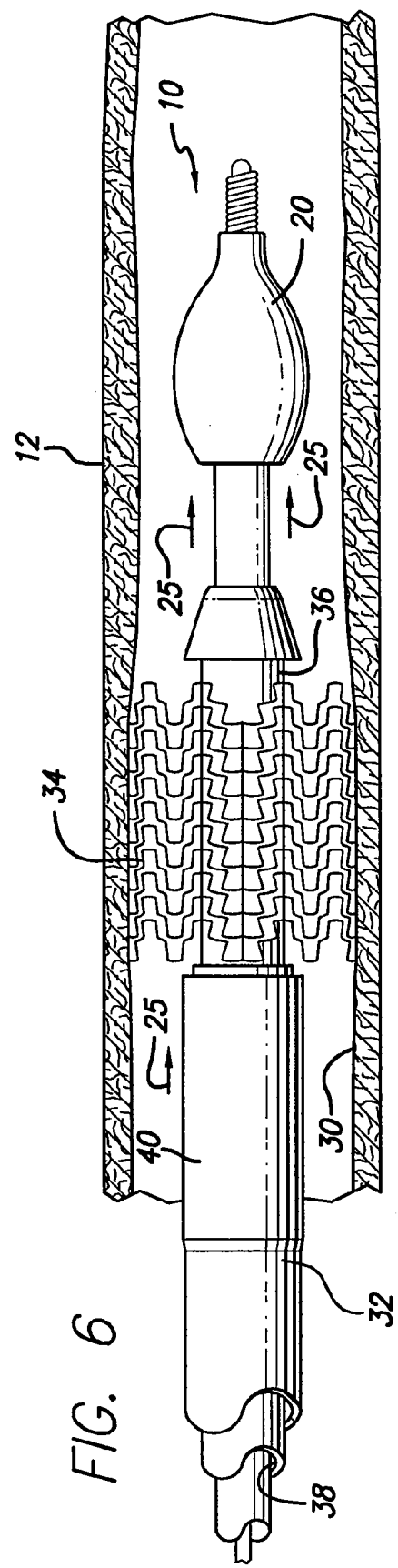

EMBOLIC PROTECTION GUIDE WIRE

CROSS-REFERENCE TO RELATED APPLICATIONS

This application is a continuation of U.S. Ser. No. 11/114,932, filed Apr. 26, 2005 now U.S. Pat. No. 7,537,598 which is a continuation of U.S. Ser. No. 09/615,157, filed Jul. 13, 2000, U.S. Pat. No. 6,964,670, issue date of Nov. 15, 2005. The contents of which are hereby incorporated by reference.

BACKGROUND OF THE INVENTION

This invention relates to a device for, and methods of, trapping and removing emboli in a body vessel. The device and method of this invention are especially adapted to be used in preventing emboli in blood from passing through a vessel such as an artery.

In recent years, numerous procedures have been adapted for expanding blood vessels (e.g. arteries), at the positions of lesions in the blood vessels, so that blood can flow through the blood vessels without obstruction from the lesions. In the process of expanding such blood vessels at the positions of the lesions, embolic particles/debris may become detached from the lesions and enter the bloodstream and subsequently migrate through the patient's vasculature to cut off or reduce the amount of oxygenated blood being supplied to sensitive organs such as the brain and heart, which may induce trauma.

Procedures have also been adapted in recent years for preventing embolic debris from flowing through the vessels in the direction of the blood flow. For example, filters have been provided for trapping the emboli. When lesions develop in the carotid artery of a patient, the placement of a filter in the patient's vasculature can somewhat reduce the movement of emboli to blood vessels leading to the patient's brain, thereby preventing strokes from occurring.

Such filters are usually delivered in a collapsed position through the patient's vasculature and are then expanded once in place in the patient's blood vessel to trap the emboli. After emboli have been trapped, the filter is collapsed and removed (with the trapped emboli) from the vessel. Unfortunately, it is possible for some of the trapped emboli to escape from the filter during the time that the filter is being collapsed and/or removed from the blood vessel. When an interventional procedure is being performed in a carotid artery, even a trace release of emboli can be damaging. For these reasons, attempts to treat lesions in the carotid arteries have been somewhat limited due to the danger presented if all of the embolic debris is not collected during the procedure.

Therefore, in light of the above, it would be desirable for a device and method which can be utilized to treat an occluded vessel and trap any emboli that may be formed during the vascular procedure. Such a device and method must also prevent the emboli from escaping from the filter during the time that the filter is being collapsed and/or removed from the blood vessel (e.g. the carotid arteries). Although considerable progress has been made in recent years in providing a satisfactory filter, it would still be desirable to provide a filter which is simple, cost efficient and trustworthy in construction, is easy to deploy and remove from the patient's vasculature with little or no adverse impact or immunological response to the patient. Also, such a device should have a thin profile to reach tight distal lesions in the patient's vasculature.

SUMMARY OF THE INVENTION

The present invention is directed to a filtering device for trapping and removing emboli from a body vessel (e.g. an artery). In one embodiment of the invention, a sheath attached to a guide wire maintains a filtering assembly in a collapsed position until the filtering assembly is ready to be deployed in the patient's vasculature. The filtering assembly is attached to a tubular shaft member which is slidable over the guide wire to move the filtering assembly out of the sheath when the filtering assembly is to be deployed and to retract the sheath back over the filtering assembly when the assembly is to collapsed and removed from the vessel. The filtering assembly may be formed from a plurality of angularly spaced splines and a filter member made from mesh or other suitable filtering material. The filter member is disposed on the splines and has properties of passing fluid in the vessel while blocking the passage of emboli in the fluid. The splines may be made from a shape-memory material which allows the spines to self expand once the sheath is removed. The spines expand against the wall of the vessel when released from the collapsed or compressed position to deploy the filter member in the vessel in order to provide the necessary emboli filtration within the vessel.

An interventional device, such as an expandable member (e.g., a stent delivery catheter) and a stent, can be disposed in the vessel to treat the lesion and open the vessel at the lesion position. Any suitable interventional device can be used with the present invention. After the interventional device has performed the procedure, the embolic protection filter is collapsed and removed from the vessel. Emboli created during the interventional procedure are released into the fluid flow (e.g. bloodstream) and are trapped within the filtering assembly.

In one aspect of the invention, the tubular shaft member can be made from a nickel titanium (NiTi) hypotube. The splines can also be made from a nickel-titanium (NiTi) alloy or other shape memory material. The spines are biased to the deployed or expanded position so that once the sheath is removed, the spines will expand radially outward to abut against the wall of the vessel to provide a tight seal which prevents fluid and emboli from passing between the filter member and vessel wall. When the device is to be collapsed and removed from the patient, the physician simply moves the sheath back over the filtering assembly causing the spines to collapse, along with the filter member, thus trapping the emboli in the filter member. The lengths of the spines and filter member should be sufficiently long so that the filtering assembly traps the emboli deep within the distal end of the filter member. This helps prevent any backflow of trapped emboli into the vessel when the filtering assembly is being collapsed. Thereafter, the entire device can be removed from the patient.

These and other advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a preferred embodiment of an embolic protection guide wire for trapping and removing emboli released in a body vessel, along with an interventional device (a stent delivery catheter and self-expanding stent), positioned within a body vessel;

FIG. 2 is an enlarged fragmentary elevational view, primarily in section, of the embodiment of FIG. 1 showing in additional detail the filtering assembly at a position in the vessel which is distal and downstream from the lesion, the filter assembly being shown covered by a sheath in the collapsed or compressed position;

FIG. 3 is an enlarged fragmentary elevational view, primarily in section, of the filtering assembly of FIG. 2, the filtering assembly being shown withdrawn from the sheath and expanded against the wall of the vessel to trap emboli in the fluid;

FIG. 4 is an enlarged fragmentary elevational view, primarily in section, of the filtering assembly in the expanded position and additionally showing the stent delivery catheter and stent in position across the lesion;

FIG. 5 is an enlarged fragmentary elevational view, primarily in section, of the filtering assembly in the expanded position and also showing the stent expanded against the vessel wall with the stent delivery catheter being withdrawn from the vessel;

FIG. 6 is an enlarged fragmentary elevational view, primarily in section, showing the filtering assembly being disposed back to the collapsed position within the sheath with the trapped emboli contained within the filter member.

DETAILED DESCRIPTION OF THE PREFERRED EMBODIMENTS

Figure 7:
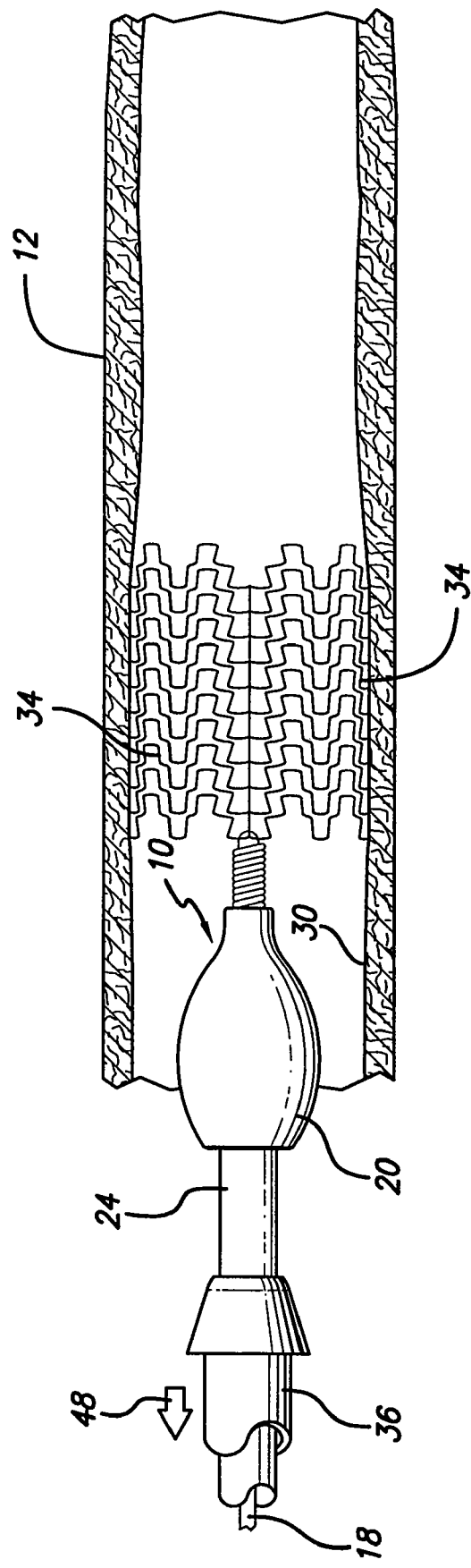
FIG. 7 is an enlarged fragmentary elevational view, primarily in section, showing the filtering assembly constricted within the sheath and being withdrawn from the vessel.

A device generally indicated at 10 and constituting one preferred embodiment of the present invention traps and removes emboli from a body vessel. The device 10 is adapted to be disposed in a blood vessel 12 to pass the fluid (blood) in the vessel and block the passage of emboli 14 (FIG. 5) in the fluid. The emboli 14 are produced when the blood vessel 12 is treated at the position of a lesion 16 during an interventional procedure such as, a balloon angioplasty procedure, a stenting procedure, an atherectomy procedure and the like. The present invention is designed to collect and remove such embolic debris from the artery to prevent the blockage of the smaller vessels downstream from the area of treatment. The device 10 is especially adapted to prevent blockage of small blood vessels leading to the brain which, if blocked, can result in the patient suffering a stroke.

The device 10 includes a flexible guide wire 18 on which is mounted a sheath 20 made from a suitable material such as a polymer, which will maintain the shape and flexibility of the sheath 20 may be dependent upon the size and location of the lesions that the sheath 20 has to cross. A filtering assembly 22 attached to a tubular shaft member 24 is disposed in a collapsed or compressed position within the sheath 20. This tubular shaft member 24 is slidably disposed on the guide wire 18 and may be made from a material such as nickel titanium (NiTi) alloy or any other material which has sufficient axial strength and flexibility to move the filtering assembly 22 along the guide wire into tortuous anatomy. For example, a hypotube made from Nitinol would be suitable since it possess sufficient strength, has adequate flexibility to be advanced through tortuous anatomy, and can be made with a thin wall to reduce the overall profile of the device. This material also is advantageous because it is able to withstand buckling.

The filtering assembly 22 is attached to the tubular shaft member 24 for slidable movement along the guide wire 18. The filtering assembly 22 may be formed from a plurality of annularly spaced splines 26 (FIG. 3) supporting a filter member 28. The filtering assembly 22 is designed to be self expanding from the collapsed position to an expanded position within the vessel 12. In the collapsed position, the filtering assembly 22 would be disposed within the sheath 20. In the expanded position, the filtering assembly 22 would flare radially outward to engage the wall 30 of the vessel 12. The splines 26 may be formed from a material having shape memory which causes the splines 26 to expand against the wall of the vessel 12 when the filtering assembly 22 is released from the sheath 20. Nitinol is one suitable material which could be used to create the splines 26. The filter member 28 may be made from a mesh or suitable filtering material. For example, the filter member 28 may be made from a thin polymer having small openings to pass the fluid in the vessel 12 while blocking the passage of the emboli 14 in the fluid. The filter member 28 may be coated with an anti-thrombotic agent to minimize blockage of the filter media by thrombosis. The filter material could also be non-porous. The ability of the embolic protection guide wire and filter to deploy and retract multiple times could allow the physician to periodically retract the device to allow blood flow downstream from the filer. Such non-porous materials would include polymeric materials well-known in medical catheter design. Each of the splines 26 could be positioned in a recess 31 formed on the tubular shaft member 24 when in the collapsed position to reduce the overall profile of the filtering assembly.

An interventional device, such as a stent delivery catheter 32 and a self-expanding stent 28, can be utilized to treat the lesion 16 and open up the artery 12 to increase blood flow therethrough. This stent delivery catheter 32 and the stent 34 may be constructed in a manner well known in the art. It should be appreciated that other interventional devices can be used with the embolic protection guide wire. For example, balloon expandable stents, balloon angioplasty catheters, atherectomy devices and the like can be used to treat the stenosis as well.

The delivery catheter 32 and the stent 34 may be disposed at the position of the lesion 16 as shown schematically in FIGS. 1 and 4-6. In the drawings, small arrows 25 indicate the direction of the fluid flow within the vessel 12. The stent delivery catheter 32 includes an inner tubular member 36 onto which the compressed or collapsed stent 34 is mounted. This inner tubular member 36 includes an inner lumen 38 which allows the stent delivery catheter 32 to be disposed over the device 10 in a co-axial arrangement. This allows the stent delivery catheter 32 to be delivered to the area of treatment using over-the-wire techniques. An outer restraining sheath 40 extends over the inner tubular member 36 in a co-axial arrangement and is used to restrain the collapsed stent 34 until it is ready to be deployed. Both the outer retraining sheath 40 and inner tubular member 36 have proximal ends (not shown) which extent outside of the patient. In use, the physician moves the proximal ends to retract the restraining sheath the necessary length to deploy the self-expanding stent 34. Once the stent is positioned across the lesion 16, the restraining sheath 40 can be retracted to expose the stent 34 and allow it to self expand against the wall 30 of the vessel 12. The opening in the vessel 12 is maintained by the stent 34 even after the delivery catheter 32 is withdrawn from the vessel 12.

The filtering assembly 22 is initially provided in the collapsed position within the sheath 20 as is shown schematically in FIGS. 1 and 2. As a first step, the filter assembly 22 is disposed in the vessel 12 to a position past the lesion 16 in the direction of the fluid flow (downstream of the lesion 16). When the filtering assembly 22 has been properly positioned in the vessel 12, the sheath 20 is moved in a direction to expose the filtering assembly 22. This causes the splines 26 and the filter member 28 to expand against the wall of the vessel 12. This is shown schematically in FIG. 3. In this position, the filter member 28 passes the fluid in the vessel 12 but blocks the passage of the emboli 14 in the fluid. The direction of the fluid flow in the vessel 12 is indicated schematically by solid arrows 25.

The stent delivery catheter 32 and stent 34 are then positioned in the vessel 12 across the lesion 16. This is shown schematically in FIG. 4. The stent 34 expands against the wall of the vessel 12, thereby opening the vessel at the position of the lesion 16 to increase the flow of fluid through the vessel. The expansion of the stent 34 against the wall of the vessel 12 is indicated schematically in FIG. 5. As indicated schematically in FIG. 5, the lesion 16 is compressed against the wall 30 of the vessel 12, thereby expanding the opening in the vessel at the position of the lesion 16.

The expansion of the stent 34 against the lesion 16 may create emboli 14 as indicated schematically in FIG. 5. However, the emboli 14 are blocked by the filter member 28 from flowing through the mesh. When all of the emboli 14 have flowed to the filter member 28, the stent delivery catheter 32 is withdrawn. This is indicated schematically in FIGS. 6 and 7.

The filtering assembly 22 (with the trapped embolic debris retained by the filter member 28) is then moved in a direction to dispose the filtering assembly 22 back into the sheath 20. When this occurs, some buckling of the filtering assembly 22 and the tubular shaft member 24 may take place. As previously indicated, the tubular shaft member 24 and the splines 26 may be made from a suitable material such as a nickel titanium alloy. This material is advantageous because it has an ability to withstand buckling when the tubular shaft member 24 and the filtering assembly 22 are pushed back into the sheath 20. It should be appreciated that the filtering assembly 22 can also be made from any metal or polymer which has flexible properties and properties of withstanding buckling when being pushed back into the sheath 20.

The sheath 20 can be provided with a variable length to ensure that all of the embolic debris remains in the sheath when the tubular shaft member 24 and the filtering assembly 22 are pushed back into the sheath 20. The lengths of the spines and filter member should be sufficiently long so that a deep pocket is created that traps the emboli deep within the distal end of the filter member 28. This helps prevent any backflow of trapped emboli 14 into the vessel when the filtering assembly 22 is being collapsed. The sheath 20 may have a slightly flared proximal end 44 which helps to receive the distal end 46 of the filtering assembly 22. After the tubular shaft member 24 and the filtering assembly 22 have been pulled back into the sheath 20, the filtering assembly 22 can be withdrawn from the vessel 12. This is indicated schematically by a hollow arrow 48 in FIG. 7.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. A device for preventing emboli in fluid passing through a body vessel of a patient, comprising:
   a guide wire having a proximal end and a distal end, the proximal end being disposed outside of the patient during usage; and
   a tubular shaft member having a lumen, a proximal end and a distal end, the proximal end of the tubular shaft member being disposed outside of the patient during usage, the guide wire being disposed within the lumen of the tubular shaft member in a co-axial arrangement, the tubular shaft member being rotatable and slideably disposed on the guide wire, the tubular shaft member including a filtering assembly movable between a collapsed position and an expanded position, the filtering assembly including a plurality of splines made from a portion of the tubular member, each spline being movable into a recess formed on the tubular member, the splines having a filter member attached thereto, the filter member having an inlet opening for receiving body fluid and a plurality of openings that allow the passing of body fluid in the body vessel while blocking the passage of emboli in the vessel.

2. The filtering device of claim 1, wherein:
   the plurality of spines disposed in annularly spaced relationship to one another.

3. The filtering device of claim 2, wherein:
   one end of each of the splines extends radially outward away from the surface of the tubular shaft member when the filtering assembly is placed in the expanded position.

4. The filtering device of claim 1, wherein:
   the filtering assembly is made from a material which is self-expanding.

5. The filtering device of claim 1, further including:
   a sheath attached to the guide wire which houses the filtering assembly in the collapsed position.

6. A device for preventing emboli in fluid passing through a body vessel of a patient, comprising:
   a guide wire having a proximal end and a distal end, the proximal end being disposed outside of the patient during usage;
   a tubular shaft member having a lumen, a proximal end and a distal end, the proximal end of the tubular shaft member being disposed outside of the patient during usage, the guide wire being disposed within the lumen of the tubular shaft member in a co-axial arrangement, the tubular shaft member being rotatable and slideably disposed on the guide wire, the tubular shaft member having a self-expanding filtering assembly associated therewith, the filtering assembly including a plurality of splines made from a portion of the tubular shaft member, each spline being movable into a recess formed on the tubular shaft member, the filtering assembly being movable between a collapsed position and an expanded position; and
   a filter member attached to the filtering assembly, the filter member having an inlet opening for receiving body fluid and a plurality of openings that allow the passing of body fluid in the body vessel while blocking the passage of emboli in the vessel.

7. The filtering device of claim 6, wherein:
   the filtering assembly is biased to the expanded position.

8. The filtering device of claim 6, further including:
   a sheath attached to the guide wire which houses the filtering assembly in the collapsed position.

* * * * *